(12) United States Patent
Morhell et al.

(10) Patent No.: US 9,733,174 B2
(45) Date of Patent: Aug. 15, 2017

(54) CAPILLARY MICROVISCOMETER

(75) Inventors: Nadim Marcelo Morhell, Pcia de Rio Ne (AR); Hernán Pastoriza, Pcia de Rio Ne (AR)

(73) Assignees: COMISION NACIONAL DE ENERGIA ATOMICA, Cludad Autonoma de Buenos Aires (AR); INIS BIOTECH LLC, Milford Kent Country, DC (US); CONSEJO NACIONAL DE INVESTIGACIONES CIENTIFICAS Y TECNICAS, Cludad Autonoma de Buenos Aires (AR)

( * ) Notice: Subject to any disclaimer, the term of this patent is extended or adjusted under 35 U.S.C. 154(b) by 412 days.

(21) Appl. No.: 14/130,676

(22) PCT Filed: Jul. 5, 2012

(86) PCT No.: PCT/IB2012/053449
§ 371 (c)(1),
(2), (4) Date: Apr. 8, 2014

(87) PCT Pub. No.: WO2013/005185
PCT Pub. Date: Jan. 10, 2013

(65) Prior Publication Data
US 2014/0216140 A1    Aug. 7, 2014

(30) Foreign Application Priority Data
Jul. 7, 2011 (AR) ............................. P20110102443

(51) Int. Cl.
*G01N 11/04* (2006.01)
*G01N 11/06* (2006.01)
*G01N 11/00* (2006.01)

(52) U.S. Cl.
CPC ............. *G01N 11/04* (2013.01); *G01N 11/06* (2013.01); *G01N 2011/0026* (2013.01)

(58) Field of Classification Search
CPC . G01N 11/04; G01N 2011/0026; G01N 11/06
(Continued)

(56) References Cited

U.S. PATENT DOCUMENTS 5,376,252 A * 12/1994 Ekstrom ................ B01D 57/02
204/603
7,144,616 B1 * 12/2006 Unger ............... B01L 3/502707
137/833

(Continued)

*Primary Examiner* — Helen Kwok
(74) *Attorney, Agent, or Firm* — Knobbe, Martens, Olson & Bear LLP

(57) ABSTRACT

Low-cost and easily-operated microviscometer suitable for medical diagnosis clinical studies and other fluid tests. The equipment consists of a microchannel (2) formed by concatenated microchannels made by micro-manufacturing techniques, and a fluid column position detector inside the microchannel. The microchannels are open at one end and closed at the other end and are made of a single biocompatible material. When a liquid drop is put into the inlet of the microchannel (2), the fluid enters by capillary until the compressed air pressure equals the capillary pressure plus atmospheric pressure. The fluid transient movement from entering the channel until stopping at its balance position is analyzed thus obtaining as a result the viscosity and the capillary pressure of the liquid tested.

8 Claims, 3 Drawing Sheets

(58) Field of Classification Search
USPC ................ 73/54.07, 54.05, 54.04, 54.13
See application file for complete search history.

(56) References Cited

U.S. PATENT DOCUMENTS

| | | | | |
|---|---|---|---|---|
| 7,188,515 B2* | 3/2007 | Burns | ............... | B82Y 15/00 |
| | | | | 702/50 |
| 7,290,441 B2* | 11/2007 | Baek | ............... | G01N 11/08 |
| | | | | 73/54.09 |
| 7,730,769 B1* | 6/2010 | Kwon | ............... | G01N 11/06 |
| | | | | 73/54.05 |
| 8,549,907 B2* | 10/2013 | Tonomura | ............... | B01F 15/0264 |
| | | | | 137/561 R |
| 9,017,623 B2* | 4/2015 | Fraden | ............... | B01L 3/502784 |
| | | | | 422/502 |
| 2002/0148282 A1* | 10/2002 | Hajduk | ............... | G01N 11/06 |
| | | | | 73/54.07 |
| 2003/0041652 A1* | 3/2003 | Spaid | ............... | B01L 3/5027 |
| | | | | 73/54.05 |
| 2012/0236901 A1* | 9/2012 | Thomas | ............... | G01K 3/04 |
| | | | | 374/102 |

* cited by examiner

CAPILLARY MICROVISCOMETER

CROSS-REFERENCE TO RELATED APPLICATIONS

This application is a U.S. National Phase of International Application No.: PCT/IB2012/053449, filed Jul. 5, 2012, designating the U.S., and published in English as WO 2013/005185 on Jan. 10, 2013, which claims the benefit of Argentine Patent Application No. P20110102443 filed Jul. 7, 2011.

FIELD OF THE INVENTION

The present invention refers to a capillary microviscometer, which allows measuring the viscosity of liquids comprising a micro-manufactured microchannel (microcapillary) made of a single biocompatible material, closed at one end thereof, wherein the liquid to be measured enters through the open end driven by the capillary pressure. From the measurement of the position (and/or velocity) of the liquid meniscus versus time, it is possible to obtain the values of capillary viscosity and pressure.

BACKGROUND AND ADVANTAGES OF THE INVENTION

When studying the physical and chemical properties of a fluid, it is important to determine the viscosity thereof. To this end, viscometers are used allowing to test fluids at different flow regimes and at different flow velocities.

There are a great number of industries and research fields wherein viscosity measurement is a routine assay, for example, in petroleum refining, lubricating oils production, emulsions in the pharmaceutical industry, printing inks, diary production, among others.

In some applications, such as analysis of biological fluids, suspension particles alter fluid viscosity in relation to flow velocity. For these rheological fluids or non-Newtonian fluids, viscometers capable of reporting viscosity values for different velocity gradients are designed.

In cases where limited volume of sample is available, it is necessary to have devices that can operate with volumes less than a few micro-liters of liquid.

There are three common types of viscometers which differ by the physical principle by which they operate. The first one, referred to as Stokes-type, consists in analyzing the movement of a body within a fluid and calculating the viscosity from the drag force exerted on the body.

In the second one, which is of Rotating type, the liquid is inserted in a cavity formed by a fixed portion and a rotating cone. Cone rotation induces a rotational movement in the fluid whose viscosity can be obtained from the ratio between rotation speed and torque applied to the cone.

In the third type, referred to as capillary viscometer, the fluid moves through a capillary tube and dynamic parameters, such as position, velocity or flow rate, versus time are recorded.

Stokes-type viscometers are not capable of measuring non-Newtonian fluids due to limitations on the operating physical principle. Conventional capillary viscometers require minimum sample of about 2 milliliters and are easy to operate, but require that a known pressure difference between their ends be established, and on the other hand, are often not suitable for measuring non-Newtonian fluids. Rotary viscometers can measure viscosities at different velocities to characterize non-Newtonian fluids, and on the market there are versions that operate with about 200-microliter samples, though their operation requires greater training and skills.

There are a number of patent documents related to viscometers. The closest to the present invention is disclosed in U.S. Pat. No. 7,188,515, differing from the present invention in several aspects, particularly, in that the device described in such patent is based on the fluid velocity analysis in a capillary open at both ends, requiring an additional capillary to measure capillary pressure. The present invention refers to a single closed capillary, where the dynamics of fluid motion is described by other equations. As provided by the present invention, it is possible to simplify the manufacture of these devices, maintaining the advantage of being able to analyze liquid volumes less than one micro-liter.

On the other hand, the device of the present invention is more reliable as to the measurements made since in the viscometer reported in U.S. Pat. No. 7,188,515, viscosity is obtained by measuring two separate parameters (capillary velocity and pressure), one of which (capillary pressure) presents wide result scatter because it greatly depends on manufacturing conditions.

Such US patent provides a micromachined capillary viscometer, where the liquid flow is driven by capillary pressure. However, there are significant differences listed as follows: 1) The liquid to be measured moves along a capillary with both ends open; 2) Capillary pressure is determined by observing how far the liquid enters a capillary of known volume; 3) Liquid velocity measurement is performed with electrical contacts spaced along the capillary; 4) It is manufactured with a glass wafer and a silicon wafer welded together; in the present invention both caps are manufactured in the same material; and 5) Temperature control of the fluid to be measured is not considered.

It can be also mentioned the device described in Japanese patent JP 61-161437 (A), wherein viscosity of the liquid is determined by measuring the fall speed of a bar of known dimensions and density immersed in the liquid to be tested. It differs from the present invention in that the operation principle is different because it is not a capillary but a Stokes-type viscometer, wherein the liquid to be measured is resting. Moreover, it is not a micromachined device.

Also, in the *Revista Chilena de Tecnología Médica*, volume 13, No. 1 pages 617-623, 1990, an article on human blood viscosity and the implementation of a simple method for whole blood and plasma—normal values—is disclosed. In that article, viscosity measurements are performed in human blood from various patients. For this, a device previously reported by B. Pirofsky in the scientific article: "The determination of viscosity in man by method based on Poiseuille's law." J. Clin. Invest. 32, 292-298, 1953, is used. It applies the principle of determining viscosity from the time a known volume of liquid takes to move along a capillary of known size. Such disclosure differs from the invention herein in the following aspects: a) It requires a large amount of sample: 2.5 ml; b) the pressure difference driving the liquid is provided by gravity, and capillary effects are neglected; c) The liquid flows in a tube open at both ends, d) Flow rate is determined by knowing the initial volume of the liquid and measuring the time of passage through the given capillary, and e) It is neither micromachined nor able to be integrated into a semiautomatic device.

With respect to U.S. Pat. No. 6,412,336 B2, which discloses apparatuses which determine a liquid viscosity by its flow velocity through a capillary tube of known dimensions, it differs from the present invention in that: a) The liquid flows through a tube open at both ends; b) the pressure difference which drives liquid movement is given by gravity and capillary effects are neglected; and c) The liquid flow rate is determined by measuring the weight of the liquid spilled versus time.

As to U.S. Pat. No. 4,441,358, it relates to apparatuses which determine liquid viscosity by its flow velocity through a capillary tube of known dimensions. It differs from the present invention in that: 1) The liquid flows through a tube open at both ends; 2) The pressure difference which drives liquid movement is given by gravity and capillary effects are neglected; and 3) The liquid flow rate is determined by measuring the time taken by the meniscus of the liquid to move between two known points of the capillary. This is detected by means of ultrasonic sensors.

In U.S. Pat. No. 4,648,262 the liquid viscosity is determined by measuring the fall speed of a sphere of known dimensions and density immersed in the liquid to be tested which is within a capillary. It differs from the present invention in that: 1) The operating principle is different (it is not a capillary but a Stokes-type viscometer) wherein the liquid to be measured is resting; 2) There is no micromachining.

With respect to U.S. Pat. No. 2,095,282, it discloses apparatuses that determine fluid viscosity by its flow velocity through a capillary tube of known dimensions. It differs from the present invention as follows: 1) The liquid flows through a tube open at both ends; 2) The pressure difference which drives liquid movement is given by gravity and capillary effects are neglected; and, 3) The liquid flow rate is determined by measuring the emptying time of predetermined volumes of liquid.

As disclosed in U.S. Pat. No. 6,470,736 B2, the apparatus measures liquid viscosity from the mass flow velocity of the liquid through a capillary tube of known dimensions. It differs from the present invention herein in that: 1) The liquid flows through a tube open at both ends; 2) The pressure difference which drives liquid movement is given by gravity and capillary effects are neglected; and, 3) The liquid flow rate is determined by measuring the weight of the liquid spilled versus time.

There are additionally other scientific works and patents related to devices with comparable characteristics to the viscometer of the present invention, such as those disclosed in patents U.S. Pat. Nos. 6,023,961, 6,402,703, 6,412,336, 6,428,488, 6,443,911, 6,692,437, 7,207,939, 6,796,168 and US 2006/0179923. Most of these devices use the same operating principle but with different methods of fluid handling and subsequent detection.

The operating principle of capillary viscometers consists in establishing a pressure difference and recording position and/or velocity of the liquid column through a capillary tube. For measuring non-Newtonian fluids it is necessary to change the pressure difference or change the capillary diameter.

Position recording is usually carried out with optical detectors (CCD cameras or photodetector array) or capacitive detectors. Capillary micromachining allows the use of small fluid samples, as shown in US 2006/0179923 A1 and US 2009/0203643 A1.

The operating principle of the present viscometer consists in profiting from capillary pressure to establish the pressure difference that moves fluid. Position is detected in relation to time and by processing data, fluid viscosity is calculated.

This flow velocity is not constant and decreases as the fluid enters the channel. Thus, the measurement of Non-Newtonian fluids can be conducted by analyzing different sections of the same capillary or machining adjacent capillaries of different diameters.

The proposed viscometer consists of sensor base, with integrated electronics which performs data processing and by interchangeable microchannels fixed in this base prior to each measurement. Optionally data can be extracted from the processor to a computer. Operating the equipment is easy since it is only required to deposit a drop in the microchannel inlet.

The device of the present invention comprises a microchannel micromachined on a single material, leaving one end of the capillary open and the other one closed, so that liquid keeps entering until the pressure exerted by the compressed air volume equals the sum of capillary pressure and atmospheric pressure.

The geometry proposed for this viscometer generates a fluid dynamic which allows achieving absolute viscosity measurement. On the other hand, the use of a single material for manufacturing microchannels ensures uniform boundary conditions along the perimeter of the channel. Conventional capillary viscometers analyze Poiseuille flows, i.e., liquid flow through an open channel at both ends and subjected to pressure difference. In this case, the closed channel modifies Poiseuille flow and another dynamics governs the movement of fluid from entering until stopping.

This device is novel by the physical principle used, in which the transient state of a liquid entering a closed channel is measured. Viscosity measurements are absolute and do not require calibration liquid in each assay. The device has been designed with temperature control and an automatic data processing system to make it easier for non-experts to use.

Despite the fact the measurement concept is similar to that presented in patent application US 2006/0179923, the present invention is clearly different due to the fact it uses a single channel to perform the measurement, it does away with the need of a reference fluid, since viscosity measurements are absolute, and it studies and analyzes fluid dynamics in a different manner. Moreover, there is a fundamental difference in the manufacturing process, using a single biocompatible material in the entire process.

BRIEF DESCRIPTION OF THE DRAWINGS

For a better understanding of the subject matter of the present invention, the same has been illustrated with schematic figures, in a preferred embodiment thereof, which are to be taken as demonstrative examples, wherein.

Figure 1:
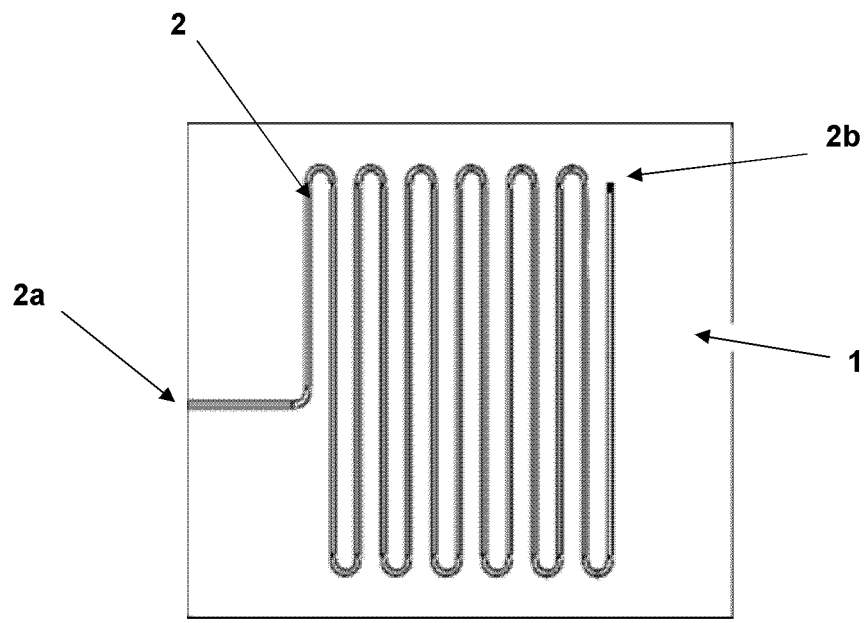
FIG. 1 illustrates a scheme of a microchanneled wafer.

In all the figures, equal reference numerals correspond to equal elements of the invention.

DETAILED DESCRIPTION OF THE INVENTION

FIG. 1 shows a micromachined wafer 1, preferably made of glass or other biocompatible material, with a single microchannel 2, open at end 2a and closed at the other end 2b, formed by microchannels concatenated preferably zigzag-shaped, located horizontally-wise, this geometry permitting to reduce the size of sensor base 3.

Figure 2:
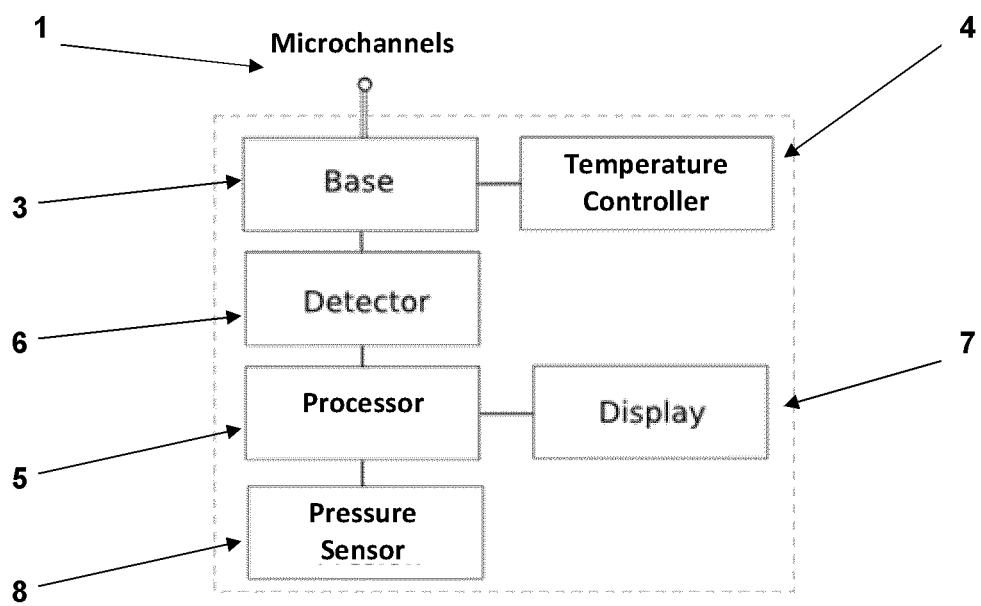
FIG. 2 shows a block diagram of the microviscometer of the present invention.

In FIG. 2 the block diagram of the sensor system shows the interconnection between the microviscometer various stages or parts. Base 3 is integral with or attached to the thermal actuator of temperature controller 4, the data processing unit 5 controls the detector system 6, the measurement of atmospheric pressure 8 and the screen or display 7.

Figure 3:
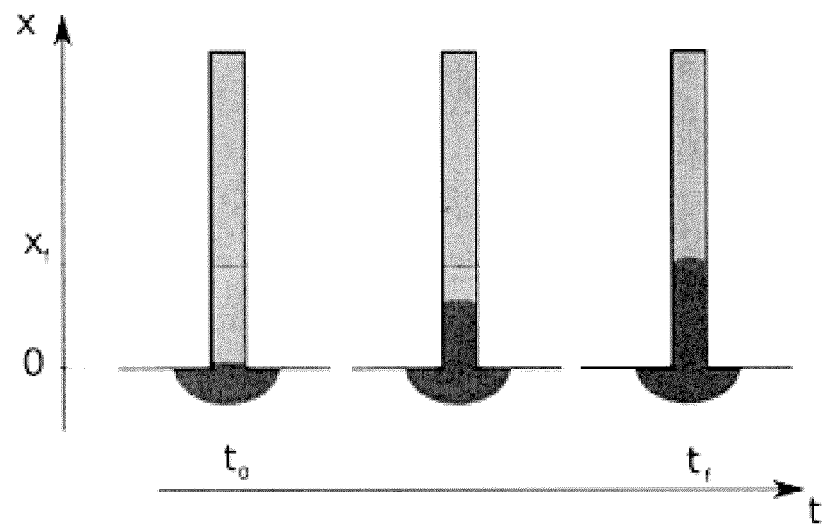
FIG. 3 presents schemes of the dynamics of a liquid drop entering a closed channel.

In FIG. 3, a liquid drop is introduced at inlet 2a of the closed microchannel, and it is shown schematically the entry of the drop at different times to reach a final position. Position "x" of the meniscus of the liquid column in relation to time "t" is expressed by the differential equation:

$$\frac{dx}{dt} = \frac{r^2}{\alpha \mu} \left( \frac{L_T(P_C - P_0) - L(P_C - P_0)}{(L_T - L)} \right)$$

Where $$L = \frac{P_C L_T}{(P_0 + P_C)}$$

is the maximum length up to which the liquid enters within microchannel 2, r is the average channel radius, α is a parameter unequivocally determined by the section of microchannel 2 (microcapillary), μ is the liquid viscosity, $L_T$ is the total channel length, $P_C$ is the capillary pressure and $P_0$ is the atmospheric pressure.

The differential equation result is:

$$t = \frac{\alpha \mu}{r^2} \frac{(L_T - L)}{L_T P_0} \left( \frac{1}{2} x^2 - (L_T - L)x + L(L_T - L)\ln\left(1 - \frac{x}{L}\right) \right)$$

where it is observed that the final position the fluid reaches is achieved when the logarithm argument is null (zero).

From this equation, it can be seen that there are only two parameters determined by the liquid and their interaction with the capillary: μ and L, and both can be determined from the measurements of x in relation to time. These data are subjected to a non-linear least squares adjustment, being μ and L the only free parameters.

Figure 4:
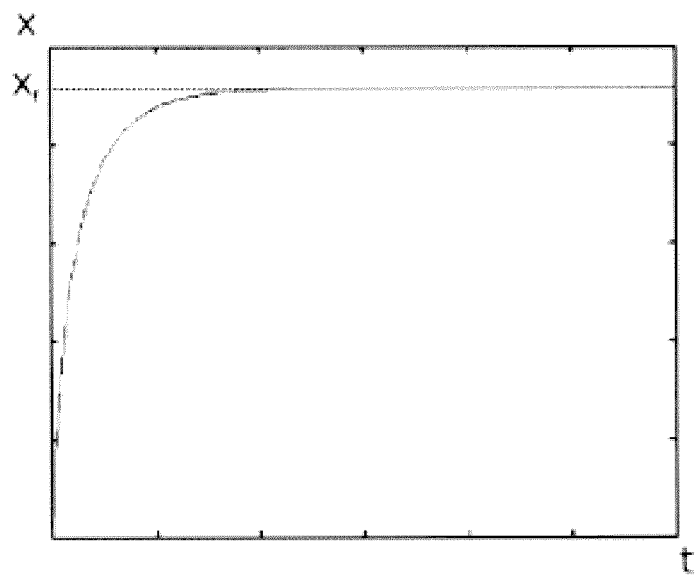
FIG. 4 illustrates the graphical result of a numerical simulation for the dynamics of the present invention.
Figure 5:
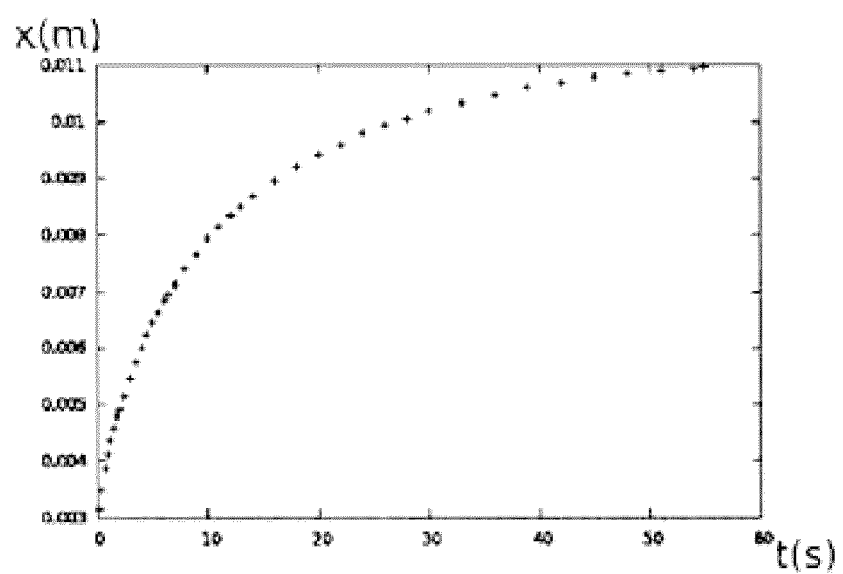
In FIG. 5 the measurement of a referenced fluid shows the same behavior as the numerical simulation.

FIG. 4 shows a graphical result of a numerical simulation of a fluid drop entering a cannel with the design dimensions and FIG. 5 shows such reference fluid measurements using an optic detection system.

It is worth pointing out that the channel concatenated zigzag-shape makes it possible to perform an optical detection with a fixed optical system that makes the most of the vision field provided by the lens.

What is claimed is:

1. A capillary microviscometer comprising:
a wafer within which only one microchannel is formed, the only one microchannel being open at one end and closed at the remaining end and formed by micromachined concatenated microchannels;
a base; and
a sensor device configured to measure a position of a fluid column within the microchannel, the sensor device being located in the base and capable of recording the dynamics of a fluid entering said only one microchannel;
the sensor device being connected to a data processor, the data processor comprising a display, wherein the processor calculates a viscosity from a transient dynamics analysis of the fluid entering the microchannel by capillary action, by detecting position x of the fluid inside the microchannel (2) in relation to time t, from the equation:

$$t = \frac{\alpha \mu}{r^2} \frac{(L_T - L)}{L_T P_0} \left( \frac{1}{2} x^2 - (L_T - L)x + L(L_T - L)\ln\left(1 - \frac{x}{L}\right) \right)$$

where L is a maximum length up to which the fluid enters within the microchannel, r is the average channel radius, α is a geometrical factor determined by the section of the microchannel, μ is the viscosity, $L_T$ is the total channel length of the microchannel, and $P_0$ is the atmospheric pressure.

2. The capillary microviscometer of claim 1, wherein the concatenated microchannels are concatenated in a zigzag shape.

3. The capillary microviscometer of claim 1, wherein the wafer is made of a single micromachined biocompatible material.

4. The capillary microviscometer of claim 1, wherein a diameter of the microchannel is such that the fluid moves within the microchannel by capillary action.

5. The capillary microviscometer of claim 2, wherein the microchannel is placed horizontally.

6. The capillary microviscometer of claim 1, wherein the base is integrated with or attached to a thermal actuator of a temperature controller.

7. The capillary microviscometer of claim 1, wherein the sensor device is an optical sensor.

8. The capillary microviscometer of claim 1, wherein the sensor device comprises an atmospheric pressure sensor.

* * * * *